United States Patent
Datta et al.

(10) Patent No.: US 8,206,366 B2
(45) Date of Patent: Jun. 26, 2012

(54) CONVERTIBLE DIAPER/PANT WITH EASE OF APPLICATION

(75) Inventors: Paul Joseph Datta, Appleton, WI (US); Michael Francis Drymalski, Appleton, WI (US); Kristi Jo Bryant, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1713 days.

(21) Appl. No.: 10/011,085

(22) Filed: Dec. 7, 2001

(65) Prior Publication Data
US 2002/0183712 A1 Dec. 5, 2002

Related U.S. Application Data (60) Provisional application No. 60/272,548, filed on Mar. 1, 2001.

(51) Int. Cl.
*A61F 13/15* (2006.01)
*A61F 13/20* (2006.01)

(52) U.S. Cl. ........... 604/385.29; 604/385.3; 604/385.25; 604/385.24

(58) Field of Classification Search .. 604/385.24–385.3, 604/386, 389–391, 393–396, 385.21–385.23
See application file for complete search history.

(56) References Cited

U.S. PATENT DOCUMENTS

| | | | |
|---|---|---|---|
| 1,975,688 A * | 10/1934 | Graves | 2/402 |
| 3,397,696 A * | 8/1968 | Rickard | 604/396 |
| 3,860,003 A * | 1/1975 | Buell | 604/385.25 |
| 4,050,462 A * | 9/1977 | Woon et al. | 604/365 |
| 4,355,425 A | 10/1982 | Jones et al. | |
| 4,515,595 A * | 5/1985 | Kievit et al. | 604/385.3 |
| 4,661,102 A * | 4/1987 | Shikata et al. | 604/385.25 |
| 4,663,220 A * | 5/1987 | Wisneski et al. | 428/221 |
| D290,780 S | 7/1987 | Wistrand | |
| 4,690,681 A * | 9/1987 | Haunschild et al. | 604/396 |
| 4,704,115 A * | 11/1987 | Buell | 604/385.26 |
| 4,981,747 A | 1/1991 | Morman | |
| 5,032,450 A | 7/1991 | Rechlicz et al. | |
| 5,061,261 A | 10/1991 | Suzuki et al. | |
| 5,106,385 A | 4/1992 | Allen et al. | |
| 5,114,781 A | 5/1992 | Morman | |
| 5,116,662 A | 5/1992 | Morman | |
| 5,151,092 A * | 9/1992 | Buell et al. | 604/385.3 |
| 5,163,932 A | 11/1992 | Nomura et al. | |
| 5,169,712 A | 12/1992 | Tapp | |
| 5,176,672 A * | 1/1993 | Bruemmer et al. | 604/385.19 |
| 5,187,952 A * | 2/1993 | Zafiroglu | 66/192 |

(Continued)

FOREIGN PATENT DOCUMENTS

EP 0 235 014 7/1991

(Continued)

*Primary Examiner* — Tatyana Zalukaeva
*Assistant Examiner* — Susan Su
(74) *Attorney, Agent, or Firm* — Dority & Manning, P.A.

(57) ABSTRACT

A pant-like, prefastened, disposable absorbent article having two leg openings which are directly below and visible through a waist opening. The waist opening has a relaxed waist opening measurement or relaxed waist diameter that is greater than a width of a chassis of the absorbent article in a crotch region. As such, the wearer's legs are positioned within and through the leg openings for easy application of the pant-like prefastened, disposable absorbent article. After initial application of the absorbent article, a waist size adjustment feature allows the waist perimeter dimension to be adjusted to conform the waist opening to the waist of the wearer.

27 Claims, 5 Drawing Sheets

U.S. PATENT DOCUMENTS

| | | |
|---|---|---|
| 5,196,000 A | 3/1993 | Clear et al. |
| 5,208,098 A | 5/1993 | Stover |
| 5,221,274 A | 6/1993 | Buell et al. |
| 5,226,992 A | 7/1993 | Morman |
| 5,234,423 A | 8/1993 | Alemany et al. |
| 5,238,733 A | 8/1993 | Joseph et al. |
| 5,242,436 A | 9/1993 | Weil et al. |
| D341,197 S | 11/1993 | Patterson |
| D342,786 S | 12/1993 | De Gooijer |
| D343,681 S | 1/1994 | Hull |
| 5,294,478 A | 3/1994 | Wanek et al. |
| 5,304,161 A | 4/1994 | Noel et al. |
| 5,312,387 A | 5/1994 | Rossini et al. |
| 5,320,891 A | 6/1994 | Levy et al. |
| 5,336,545 A | 8/1994 | Morman |
| 5,358,500 A | 10/1994 | Lavon et al. |
| 5,366,451 A | 11/1994 | Levesque |
| 5,368,584 A | 11/1994 | Clear et al. |
| 5,370,634 A | 12/1994 | Ando et al. |
| 5,383,871 A | 1/1995 | Carlin et al. |
| 5,393,599 A | 2/1995 | Quantrille et al. |
| 5,407,507 A | 4/1995 | Ball |
| 5,409,761 A | 4/1995 | Langley |
| H1440 H | 5/1995 | New et al. |
| 5,413,811 A | 5/1995 | Fitting et al. |
| D361,839 S | 8/1995 | Doss |
| 5,439,458 A | 8/1995 | Noel et al. |
| 5,454,803 A | 10/1995 | Sageser et al. |
| 5,466,513 A | 11/1995 | Wanek et al. |
| 5,482,765 A | 1/1996 | Bradley et al. |
| 5,492,753 A | 2/1996 | Levy et al. |
| 5,496,298 A | 3/1996 | Kuepper et al. |
| 5,496,429 A | 3/1996 | Hasse et al. |
| 5,507,736 A | 4/1996 | Clear et al. |
| 5,507,895 A | 4/1996 | Suekane |
| 5,509,915 A * | 4/1996 | Hanson et al. ............... 604/378 |
| 5,514,470 A | 5/1996 | Haffner et al. |
| 5,527,304 A | 6/1996 | Buell et al. |
| 5,531,732 A | 7/1996 | Wood |
| 5,540,976 A | 7/1996 | Shawver et al. |
| D372,532 S | 8/1996 | Rossini et al. |
| 5,542,942 A | 8/1996 | Kline et al. |
| 5,542,943 A | 8/1996 | Sageser |
| 5,545,275 A | 8/1996 | Herrin et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,560,974 A | 10/1996 | Langley |
| 5,569,232 A | 10/1996 | Roe et al. |
| 5,571,096 A | 11/1996 | Dobrin et al. |
| 5,575,783 A | 11/1996 | Clear et al. |
| 5,580,411 A | 12/1996 | Nease et al. |
| 5,582,903 A | 12/1996 | Levy et al. |
| 5,591,152 A | 1/1997 | Buell et al. |
| 5,595,567 A | 1/1997 | King et al. |
| 5,603,708 A | 2/1997 | Seth |
| 5,618,366 A | 4/1997 | Suekane |
| 5,622,589 A | 4/1997 | Johnson et al. |
| 5,624,420 A | 4/1997 | Bridges et al. |
| 5,624,428 A | 4/1997 | Sauer |
| 5,626,574 A | 5/1997 | Sasaki et al. |
| 5,628,737 A | 5/1997 | Dorbin et al. |
| 5,634,916 A | 6/1997 | Lavon et al. |
| 5,643,239 A | 7/1997 | Bodford et al. |
| 5,643,242 A | 7/1997 | Lavon et al. |
| H1674 H | 8/1997 | Ames et al. |
| 5,653,704 A | 8/1997 | Buell et al. |
| D383,207 S | 9/1997 | Cassell |
| 5,662,636 A | 9/1997 | Benjamin et al. |
| 5,669,897 A | 9/1997 | Lavon et al. |
| 5,674,216 A | 10/1997 | Buell et al. |
| 5,680,653 A | 10/1997 | Mathis et al. |
| H1698 H | 11/1997 | Lloyd et al. |
| 5,683,533 A | 11/1997 | Keighley et al. |
| 5,690,626 A | 11/1997 | Suzuki et al. |
| 5,690,627 A | 11/1997 | Clear et al. |
| 5,693,038 A | 12/1997 | Suzuki et al. |
| 5,695,849 A | 12/1997 | Shawver et al. |
| 5,695,868 A | 12/1997 | McCormack |
| 5,702,551 A | 12/1997 | Huber et al. |
| D389,320 S | 1/1998 | Vinnage et al. |
| 5,705,013 A | 1/1998 | Nease et al. |
| 5,709,921 A | 1/1998 | Shawver |
| 5,718,698 A | 2/1998 | Dobrin et al. |
| 5,728,451 A | 3/1998 | Langley et al. |
| 5,735,838 A | 4/1998 | Rönnberg et al. |
| 5,735,840 A | 4/1998 | Kline et al. |
| 5,749,866 A | 5/1998 | Roe et al. |
| 5,779,691 A | 7/1998 | Schmitt |
| 5,788,685 A | 8/1998 | Rönnberg et al. |
| 5,788,797 A | 8/1998 | Herrin et al. |
| 5,789,065 A | 8/1998 | Haffner et al. |
| 5,810,797 A | 9/1998 | Menard et al. |
| 5,817,081 A | 10/1998 | LaVon et al. |
| 5,830,206 A | 11/1998 | Larsson |
| D403,402 S | 12/1998 | Dreier et al. |
| D403,404 S | 12/1998 | Bernard et al. |
| 5,843,057 A | 12/1998 | McCormack |
| 5,843,066 A | 12/1998 | Dorbin |
| 5,846,232 A | 12/1998 | Serbiak et al. |
| 5,853,881 A | 12/1998 | Estey et al. |
| 5,855,574 A | 1/1999 | Kling et al. |
| 5,855,999 A | 1/1999 | McCormack |
| 5,858,292 A | 1/1999 | Dragoo et al. |
| 5,865,823 A | 2/1999 | Curro |
| 5,865,926 A | 2/1999 | Wu et al. |
| 5,876,390 A | 3/1999 | Hall et al. |
| 5,883,028 A | 3/1999 | Morman et al. |
| 5,891,120 A | 4/1999 | Chmielewski |
| 5,897,545 A * | 4/1999 | Kline et al. ................... 604/386 |
| 5,906,008 A | 5/1999 | Heki et al. |
| 5,906,604 A | 5/1999 | Rönnberg et al. |
| 5,910,225 A | 6/1999 | McAmish et al. |
| 5,913,850 A | 6/1999 | D'Alessio et al. |
| 5,914,084 A | 6/1999 | Benson et al. |
| 5,916,207 A | 6/1999 | Toyoda et al. |
| 5,921,977 A | 7/1999 | Schmitz |
| 5,925,027 A | 7/1999 | Schmitz |
| 5,926,926 A | 7/1999 | Kato |
| 5,928,209 A | 7/1999 | Bodford et al. |
| 5,932,497 A | 8/1999 | Morman et al. |
| 5,938,648 A | 8/1999 | LaVon et al. |
| 5,957,908 A | 9/1999 | Kline et al. |
| 5,989,688 A | 11/1999 | Barge et al. |
| 5,997,521 A | 12/1999 | Robles et al. |
| 6,002,064 A | 12/1999 | Kobylivker et al. |
| 6,004,306 A | 12/1999 | Robles et al. |
| 6,015,764 A | 1/2000 | McCormack et al. |
| 6,020,536 A | 2/2000 | Osterdahl et al. |
| 6,022,431 A | 2/2000 | Blenke et al. |
| 6,022,432 A | 2/2000 | Elsberg et al. |
| 6,023,789 A * | 2/2000 | Wilson et al. ..................... 2/228 |
| 6,027,484 A * | 2/2000 | Romare ....................... 604/386 |
| 6,030,372 A | 2/2000 | Buell et al. |
| D421,802 S | 3/2000 | Van Gompel et al. |
| D422,078 S | 3/2000 | Vukos et al. |
| 6,036,805 A | 3/2000 | McNichols |
| 6,050,985 A | 4/2000 | Lavon et al. |
| 6,051,094 A | 4/2000 | Melbye et al. |
| 6,086,571 A | 7/2000 | Guevara et al. |
| 6,132,411 A | 10/2000 | Huber et al. |
| 6,174,303 B1 | 1/2001 | Suprise et al. |
| 6,491,676 B1 * | 12/2002 | Suzuki et al. ............ 604/385.29 |
| 6,648,866 B2 * | 11/2003 | Magee et al. ............ 604/385.03 |

FOREIGN PATENT DOCUMENTS

| | | |
|---|---|---|
| EP | 0 233 704 | 7/1992 |
| EP | 0 400 111 | 8/1994 |
| EP | 0 691 203 | 1/1996 |
| EP | 0 707 106 | 4/1996 |
| EP | 0 780 108 | 6/1997 |
| EP | 0 570 980 | 7/1997 |
| EP | 0 597 331 | 11/1997 |
| EP | 0 757 550 | 12/1998 |
| EP | 0 880 956 | 12/1998 |
| EP | 0 587 196 | 3/1999 |

| | | |
|---|---|---|
| EP | 0 734 321 | 3/1999 |
| GB | 2288315 A * | 10/1995 |
| WO | 94/17768 | 8/1994 |
| WO | 94/18927 | 9/1994 |
| WO | 94/26222 | 11/1994 |
| WO | WO 95/06451 | 3/1995 |
| WO | WO 9513775 A1 * | 5/1995 |
| WO | 95/27460 | 10/1995 |
| WO | 95/27462 | 10/1995 |
| WO | 95/27463 | 10/1995 |
| WO | 96/01094 | 1/1996 |
| WO | 96/03101 | 2/1996 |
| WO | WO 96/03949 | 2/1996 |
| WO | 96/18367 | 6/1996 |
| WO | 96/19174 | 6/1996 |
| WO | 96/35402 | 11/1996 |
| WO | 97/23180 | 7/1997 |
| WO | 97/25951 | 7/1997 |
| WO | 98/05813 | 2/1998 |
| WO | 98/29246 | 7/1998 |
| WO | 98/29247 | 7/1998 |
| WO | 98/29479 | 7/1998 |
| WO | 98/29480 | 7/1998 |
| WO | 98/35641 | 8/1998 |
| WO | 98/51474 | 11/1998 |
| WO | 99/14262 | 3/1999 |
| WO | 99/18906 | 4/1999 |
| WO | 99/21522 | 5/1999 |
| WO | WO 99/25296 | 5/1999 |
| WO | 99/37263 | 7/1999 |
| WO | 99/37839 | 7/1999 |
| WO | 99/48452 | 9/1999 |
| WO | 99/53881 | 10/1999 |
| WO | 99/60966 | 12/1999 |
| WO | 99/60967 | 12/1999 |
| WO | 99/60968 | 12/1999 |
| WO | 99/60972 | 12/1999 |
| WO | 99/60973 | 12/1999 |
| WO | 99/60974 | 12/1999 |
| WO | 00/37010 | 6/2000 |
| WO | 00/46023 | 8/2000 |
| WO | 01/70155 | 9/2001 |
| WO | 01/82849 | 11/2001 |
| WO | 01/82850 | 11/2001 |
| WO | 01/82851 A1 | 11/2001 |
| WO | 01/82852 A1 | 11/2001 |

* cited by examiner

CONVERTIBLE DIAPER/PANT WITH EASE OF APPLICATION

CROSS REFERENCE TO RELATED APPLICATION

This application claims the benefit of U.S. Provisional Application No. 60/272,548, filed Mar. 1, 2001.

FIELD OF INVENTION

The present invention relates to a disposable absorbent article that is adapted to contain body exudates. More particularly, the present invention relates to a pant-like prefastened, disposable absorbent article having easy leg application and a desired fit range. The article is convertible between a diaper and a pull-on pant.

BACKGROUND OF THE INVENTION

Absorbent articles such as diapers, training pants or incontinence garments desirably provide a close, comfortable fit about the wearer and contain body exudates. Moreover, absorbent articles, after being soiled, optimally can be removed from the wearer in a convenient and clean manner without undesirably soiling the caregiver, the surrounding area or the clothes of the wearer. In certain circumstances, it is also beneficial for such absorbent articles to be capable of being pulled up or down over the hips of the wearer to allow the wearer or caregiver to easily pull the article on or off. Given the various shapes and sizes of the wearers of absorbent articles, it would also be beneficial for the caregiver or the wearer to be able to adjust the fit of the waist opening of the article.

Conventional diapers are not provided in a prefastened condition and have typically included a front waist portion and a back waist portion that are releasably connected about the hips of the wearer by conventional fasteners such as adhesive tape fasteners or hook and loop fasteners. For example, conventional fastening means typically included a pair of fasteners, such as adhesive tape tabs, located on the outermost corners in the back waist region of the diaper and a complimentary fastener, such as a taping panel, located on the exterior surface of the outer cover in the front waist portion of the diaper. In such a configuration, the diaper is positioned between the legs of the wearer while the wearer is lying down, and the adhesive tape tabs are releasably attached to the taping panel to secure the back waist portion to the front waist portion of the diaper, to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached. Moreover, the fasteners on such conventional diapers generally are difficult to disengage and reattach to further adjust or conform the waist opening of the diaper to the waist of the wearer. Such disengagement and reattachment can also be difficult to accomplish when the wearer is active.

Several attempts have been made to provide absorbent articles that effectively contain body exudates, which are easily pulled up and/or down over the hips of the wearer to provide for easy cleaning and removal. For example, some conventional absorbent articles, such as conventional training pants, have included integral side panels that connect the front waist portion to the back waist portion of the absorbent article. The side panels have been made to stretch such that the waist opening of the absorbent article can expand to allow the absorbent article to be pulled up or down over the hips of the wearer if desired. The side panels have also been designed so that they may be torn to remove the training pant from the wearer after it has been soiled.

However, many of these absorbent articles have not been completely satisfactory. For example, conventional absorbent articles such as training pants have a chassis with a width at a crotch region of the absorbent article at least as wide as the waist opening of the absorbent article when the absorbent article is in a relaxed, unstretched configuration. If the chassis width at the crotch region is at least as wide as the relaxed waist opening, the wearer cannot step into the leg openings and the application of the absorbent article is difficult. In this case, the wearer or caregiver must put the wearer's foot off to the side when applying the training pant.

Additionally, the absorbent articles, such as training pants, have not always been able to achieve a close conforming fit to the wearer while still being able to expand enough to be pulled up and down over the hips of the wearer. Often such training pants fit the waist of the wearer loosely, which can undesirably result in leaks. As a result, many of these articles have not contained bodily exudates as effectively as conventional diaper-type articles that can be adjusted to achieve a more conforming fit to the wearer. Moreover, the inspection and removal of soiled absorbent articles that have integral side panels, such as conventional training pants, have not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles that have a relatively narrow chassis at the crotch region for easy leg application, with the leg openings directly below and visible through the waist opening. Further, there remains a need for absorbent articles that are adjustable to conform to the wearer for effective containment of bodily exudates, are capable of being pulled up and/or down over the hips and buttocks of the wearer, are readily secured about and removed from the wearer in a convenient and clean manner and are easily inspected by the caregiver to determine whether the article is soiled. Additionally, there remains a need for absorbent articles that can be converted between pull-on pants and diapers.

SUMMARY OF THE INVENTION

In response to the difficulties and problems discussed above, new pant-like prefastened, disposable absorbent articles have been discovered having easy leg application and a desired fit range. As the mobility and activity level of a child increases, there are advantages to having access to a pant-like prefastened, disposable absorbent article that can be applied and removed both as a diaper and as a pull-on pant. Further, wearers of absorbent articles have a wide range of shapes and sizes. As babies and young children progress through the "step" sizes of absorbent articles, there is an increasing degree of differences in the body shapes of users in the higher step sizes and a corresponding need for an absorbent article that has a larger fit range.

The present invention is directed to a pant-like prefastened, disposable absorbent article that can be pulled over the wearer's hips and buttocks and positioned properly to effectively absorb and/or contain the body exudates. The pant-like prefastened, disposable absorbent article has a waist opening and two leg openings which are directly below and visible through the waist opening. As such, the wearer's legs can easily be positioned within and through the leg openings for easy application of the absorbent article.

The present invention comprehends a prefastened, refastenable absorbent article, including a chassis having a front waist region, a back waist region and a crotch region intermediate the front waist region and the back waist region. The chassis defines an elasticized waist opening having a relaxed waist opening diameter. A first side seam includes passive bonds which connect a first edge portion of the front waist region to a first edge portion of the back waist region. Similarly, a second side seam includes passive bonds which connect a second edge portion of the front waist region to a second edge portion of the back waist region. A first leg elastic member is positioned along a first side edge of the chassis at the crotch region, and a second leg elastic member positioned along a second side edge of the chassis at the crotch region. The first leg elastic member and the second leg elastic member define a crotch elastic spacing between an outside edge of the first leg elastic member and an outside edge of the second leg elastic member at a narrowest spacing of the leg elastic members in the crotch region, wherein the crotch elastic spacing is less than the relaxed waist opening diameter.

In conventional absorbent articles, such as conventional training pants, the chassis has a width at the crotch region that is at least equal to the relaxed waist opening diameter. Thus, the wearer is not able to step into and through the leg opening and application of the conventional absorbent article is difficult.

The present invention further comprehends a pants shaped prefastened, refastenable disposable absorbent article having a vertical axis. The absorbent article includes an outer cover, a bodyside liner, and an absorbent core positioned between the outer cover and the bodyside liner. The outer cover, the absorbent core and the bodyside liner define a chassis having a front waist region, a back waist region and a crotch region intermediate the front waist region and the back waist region. The absorbent article includes a first side seam including passive bonds which connect a first edge portion of the front waist region to a first edge portion of the back waist region, and a second side seam including passive bonds which connect a second edge portion of the front waist region to a second edge portion of the back waist region. A first leg elastic member is positioned along a first side edge of the chassis at the crotch region and a second leg elastic member is positioned along a second side edge of the chassis at the crotch region. The chassis forms an elasticized waist opening having a relaxed waist opening diameter greater than the crotch elastic spacing that is defined by a lateral distance between an outside edge of the first leg elastic member and an outside edge of the second leg elastic member at a narrowest spacing of the leg elastic members in the crotch region.

Table 1 below shows the desired, more desired and most desired fit range for absorbent articles for babies, according to this invention. Table 2 below shows the desired, more desired and most desired fit range for absorbent articles for adults, according to this invention.

TABLE 1

Desirable Fit Range for Infant Diaper Articles

| Diaper Step Size | Weight Range (lbs.) | Desired Fit Range (mm) | More Desirable Fit Range (mm) | Most Desirable Fit Range (mm) |
|---|---|---|---|---|
| 1 | <14 | >35 | >70 | >140 |
| 2 | 14-18 | >38 | >76 | >152 |
| 3 | 16-28 | >45 | >90 | >180 |
| 4 | 25-35 | >50 | >100 | >200 |
| 5 | >27 | >52 | >104 | >208 |
| 6 | >35 | >60 | >120 | >240 |

TABLE 2

Desirable Fit Range for Adult Pant Articles

| Pant Size | Weight Range (lbs.) | Desired Fit Range (mm) | More Desirable Fit Range (mm) | Most Desirable Fit Range (mm) |
|---|---|---|---|---|
| S/M | 115-190 | >100 | >200 | >300 |
| M/L | 170-260 | >125 | >225 | >325 |

For example, the absorbent article has a fit range desirably greater than about 50 mm, more desirably greater than about 100 mm, and most desirably greater than about 200 mm, when sized for a 25-35 pound baby, in order for the absorbent article to function as a pant-like prefastened absorbent article that is pulled on over the hips of the wearer. The lateral direction of an absorbent article having a pant-like or diaper-like configuration is the direction generally parallel to the waistline of the article. The longitudinal direction is the direction generally perpendicular to the waistline, from the front waist region to the back waist region of the article, through the crotch region.

The fit range ("FR") of the prefastened diaper 20 typically is defined as a difference between a relaxed waist opening measurement and an extended waist opening measurement, using the following equation:

$$FR = W_e - W_r;  \quad\quad\quad Eq.~(1)$$

wherein $W_e$ is the extended waist opening measurement of the diaper 20 in the prefastened configuration and $W_r$ is the relaxed waist opening measurement of the diaper 20 in the prefastened configuration. The extended waist opening measurement is a measurement of the circumference of the waist opening 33 when a tension force of about 1400 grams is applied to the diaper 20. The relaxed waist opening measurement is a measurement of the circumference of the waist opening 33 when no tension force is applied to the diaper 20. For example, desirably, the diaper 20 has an extended waist opening measurement of about 550 mm to about 750 mm and a relaxed waist opening measurement of about 350 mm to about 400 mm for a step 4 diaper prefastened. A step 4 diaper fits a baby weighing about 25 pounds to about 35 pounds. The extended waist opening measurement and the relaxed waist opening measurement can be determined using test procedure ASTM 5034 with two modifications. First, the sample is cut from a waist band about 2 inches by about 6 inches and placed in the equipment so that the elongation is in the direction that the waistband extends (6 inches). Second, the force is measured and documented at a 50 mm elongation.

DEFINITIONS

As used herein, the term "convertible" refers to an absorbent article that can be pulled on like a pant or applied as a diaper. The article can also be removed as either a pant or a diaper. The user has the option of application/removal that suits the situation.

As used herein, the term "disposable" refers to articles which are intended to be discarded after a limited use and that are not intended to be laundered or otherwise restored for reuse.

As used herein, the terms "elastic," "elasticized" and "elasticity" refer to a property of a material or composite by virtue of which the material or composite tends to recover its original size and shape after removal of a force causing a deformation.

As used herein, the term "elastomeric" refers to a material or composite which can be elongated by at least 50 percent of its relaxed length in any direction and which will recover, upon release of the applied force, at least 40 percent of its elongation. It is generally desired that the elastomeric material or composite be capable of being elongated by at least 100 percent, more desirably by at least 300 percent, of its relaxed length and recover, upon release of an applied force, at least 50 percent of its elongation.

As used herein, the term "extensible" refers to a material or composite which can be elongated by at least 50% of its relaxed length in any direction and tends not to recover, or recovers less than 40% of its elongation, after removal of a force causing a deformation.

As used herein, the term "inelastic" refers to materials which are not elastomeric, either because they cannot be sufficiently stretched by the above amount or because they do not sufficiently retract by the above amount when stretched and relaxed.

As used herein, the terms "necked" and "neck stretched" are interchangeable terms that refer to a method of elongating an inelastic nonwoven fabric, generally in the longitudinal, or machine direction of the fabric, to reduce its width in a controlled manner to a desired amount. The controlled stretching may take place under cool, room temperature, or greater temperatures, and is limited to an increase in overall dimension in the direction being stretched up to the elongation required to break the fabric, which in most cases is about 1.2 to 1.4 times an original length. The resulting neck-stretched fabric can be extended in the lateral (cross-machine) direction of the fabric during subsequent use, causing the fabric to return toward its original pre-necked configuration. Neck stretching processes are disclosed, for example, in U.S. Pat. No. 4,443,513 to Meitner et al.; U.S. Pat. Nos. 4,965,122, 4,981,747 and U.S. Pat. No. 5,114,781 to Morman; and U.S. Pat. No. 5,244,482 to Hassenboehler Jr. et al.

As used herein, the term "passive bond" refers to a bond which has a relatively low peel strength such that the bond can be easily broken by hand if desired to assist in inspecting or removing an absorbent article from the wearer, without tearing or severely damaging the other portions of the article, and without causing trauma to the wearer or spillage of waste material from the absorbent article. The passive bond itself is not refastenable.

As used herein, the term "permanently bonded" refers to the joining, adhering, connecting, attaching, or the like, of two elements of an absorbent article such that the elements tend to be and remain bonded during normal use conditions of the absorbent article.

As used herein, the term "prefastened" refers to a condition wherein the absorbent article has a fastening feature which is engaged or fastened prior to use by the wearer. For example, the fastening feature of the absorbent article may be engaged or fastened during the manufacturing process.

As used herein, the term "refastenable" refers to the property of two elements being capable of releasable attachment, separation, and subsequent releasable reattachment without substantial permanent deformation or other damage to either element.

As used herein, the term "releasably attached," "releasably engaged," and variations thereof refer to two elements being connected or connectable such that the elements tend to remain connected absent a separation force applied to one or both of the elements and the elements being capable of separation without substantial permanent deformation or other damage. The required separation force is typically beyond that encountered while wearing the absorbent article.

As used herein, the term "tension" refers to a uniaxial force tending to cause the extension of a body or a balancing force within that body resisting the extension.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 6 representatively shows a front plan view of a pant-like prefastened, disposable absorbent article having a plurality of passive bonds forming a "zig zag" bond pattern, according to one embodiment of this invention;

FIG. 7 representatively shows a perspective view of a pant-like prefastened, disposable absorbent article, according to one embodiment of this invention, having a cylindrical rod inserted therethrough; and FIG. 8 representatively shows a top plan view of a pant-like prefastened, disposable absorbent article having two leg openings directly below and visible through a waist opening of the absorbent article, according to one embodiment of this invention.

DETAILED DESCRIPTION OF THE INVENTION

The present invention is directed to a pant-like prefastened, disposable absorbent article adaptable to be worn adjacent to the body of a wearer to absorb and contain various exudates discharged from the body. The absorbent article is initially fastened, or prefastened, so the absorbent article can be pulled over the wearer's hips and buttocks and positioned properly to effectively absorb and/or contain the body exudates. The prefastened absorbent article is also refastenable such that the absorbent article can be adjusted or fit to the wearer's waist size and easily inspected to determine if the absorbent article has been soiled. For example, the pant-like prefastened, disposable absorbent article may include a waist size adjustment means which allows the wearer or the caregiver to adjust the fit of the article once it has been positioned on the hips of the wearer, without disengaging the prefastened side seams. As such, the pant-like prefastened, disposable absorbent article of the present invention can function in a similar manner to conventional training pants when left in the prefastened configuration or can be unfastened prior to or during use to function in a refastenable manner similar to a conventional diaper.

The pant-like prefastened, disposable absorbent article of the present invention will be described in terms of a pant-like prefastened, disposable diaper that is adapted to be worn by infants about the lower torso. In particular, the pant-like prefastened, disposable absorbent article will be described in terms of a pant-like prefastened, disposable diaper 20, as shown in FIGS. 1-8, having two leg openings 35 which are directly below and visible through a waist opening 33 of the diaper 20. As such, the wearer's legs are positioned within and through the leg openings 35 for easy application of the diaper 20. It is apparent that the articles and methods of the present invention are equally adaptable for other types of absorbent articles such as adult incontinent products, training pants, underpants, feminine hygiene products, other personal care or health care garments, swimwear and the like.

The diaper 20 of the present invention has a fit range desirably of at least about 50 mm, more desirably of at least about 200 mm, in order for the diaper 20 to function as a pant-like prefastened absorbent article. The fit range ("FR") of the prefastened diaper 20 typically is defined as a difference between a relaxed waist opening measurement and an extended waist opening measurement, using the following equation:

$$FR = W_e - W_r;$$ Eq. (1)

wherein $W_e$ is the circumference of the lateral extended waist opening measurement of the diaper 20 in the prefastened configuration and $W_r$ is the circumference of the lateral relaxed waist opening measurement of the diaper 20 in the prefastened configuration. The extended waist opening measurement is a measurement of the circumference of the waist opening 33 when a tension force of about 1400 grams is applied to the diaper 20. The relaxed waist opening measurement is a measurement of the circumference of the waist opening 33 when no tension force is applied to the diaper 20. For example, desirably, the diaper 20 has an extended waist opening measurement of about 550 mm to about 750 mm and a relaxed waist opening measurement of about 350 mm to about 400 mm for a step 4 diaper prefastened. A step 4 diaper fits a baby weighing about 25 pounds to about 35 pounds. The extended waist opening measurement and the relaxed waist opening measurement can be determined using test procedure ASTM 5034 with two modifications. First, the sample is cut from a waist band about 2 inches by about 6 inches and placed in the equipment so that the elongation is in the direction that the waistband extends (6 inches). Second, the force is measured and documented at a 50 mm elongation.

To provide a desired fit range, the diaper 20 must have components which are elastic or extensible in at least one desired direction, for example in a lateral or cross-machine direction. Cost-effective elastic materials, as well as additional extensible materials which do not limit or restrict the elastic materials, determine the fit range of the diaper 20. In one embodiment of this invention, the diaper 20 has an elastic fit panel and/or elastic side panels or ears to deliver the desired fit range while maintaining elastic tension forces of about 0 grams to about 1400 grams, and desirably about 100 grams to about 1400 grams during use of the diaper 20.

Figure 1:
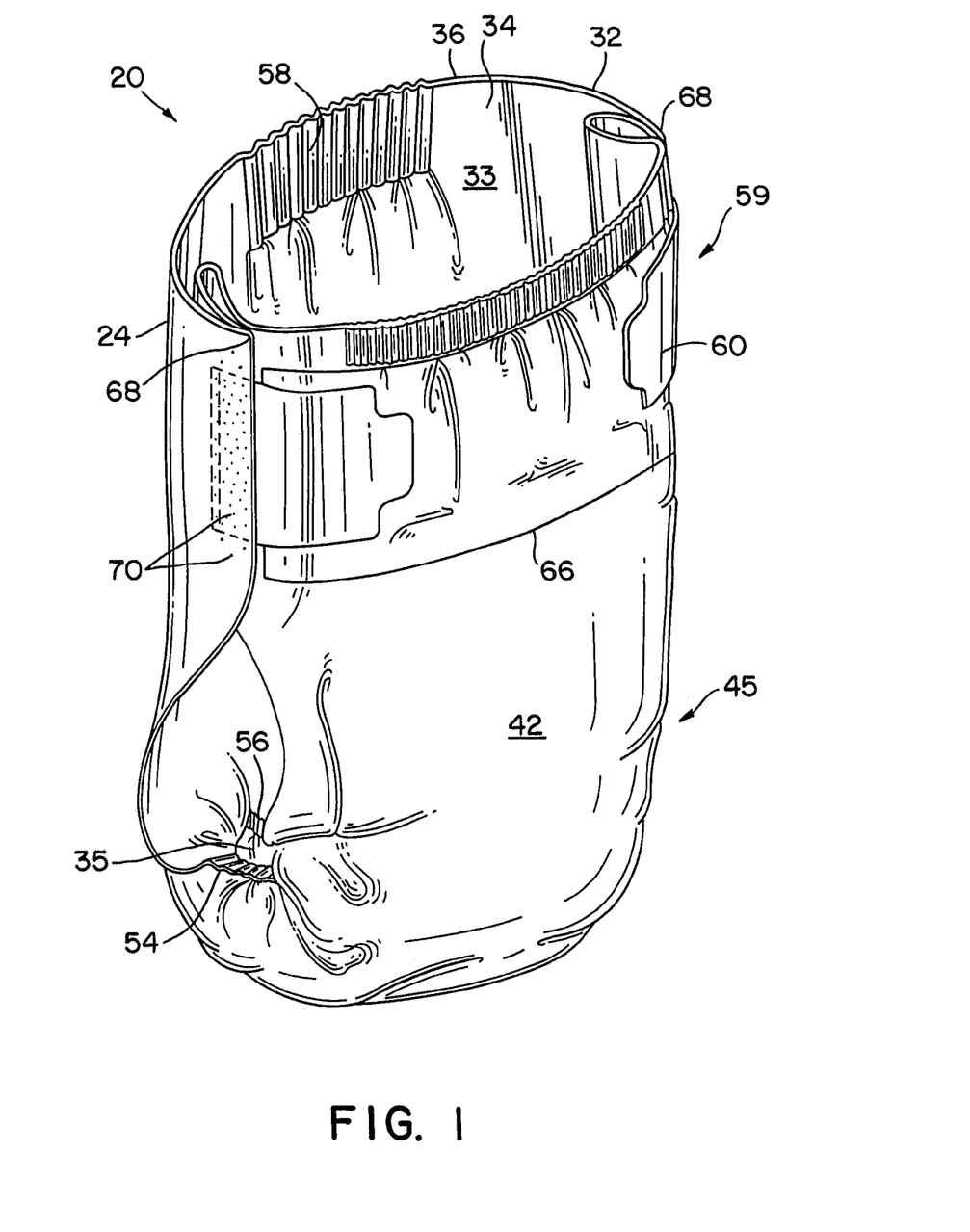
FIG. 1 representatively shows a perspective view of a pant-like prefastened, disposable absorbent article, according to one embodiment of this invention.
Figure 2:
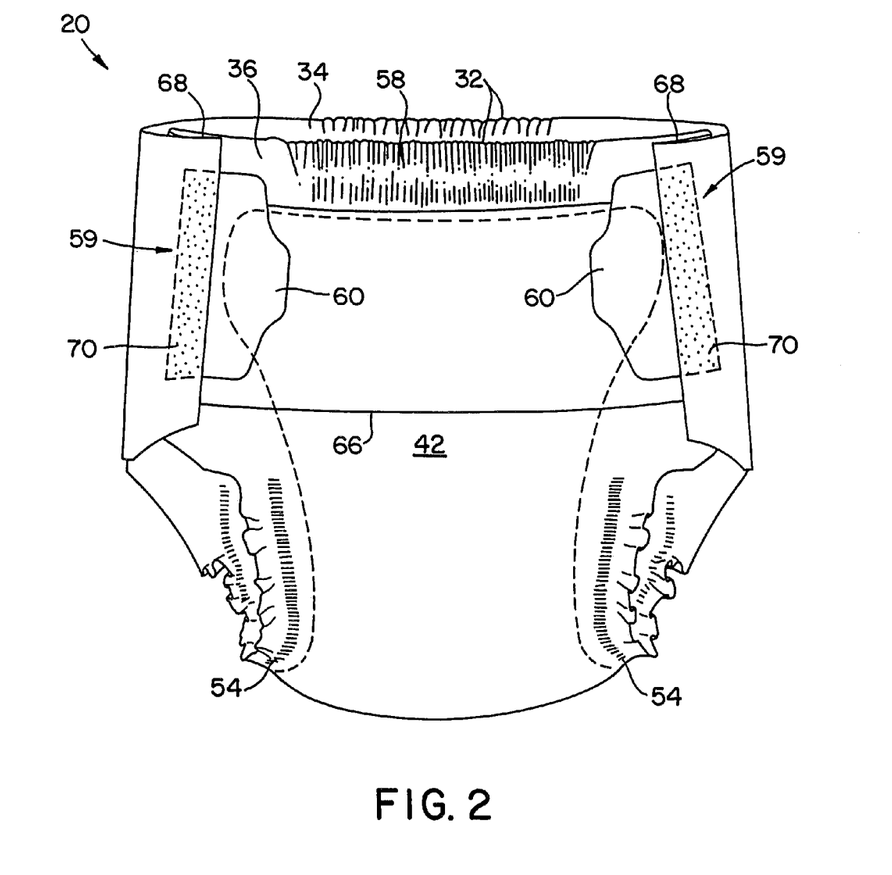
FIG. 2 representatively shows a front plan view of the pant-like prefastened, disposable absorbent article of FIG. 1, according to one embodiment of this invention.
Figure 3:
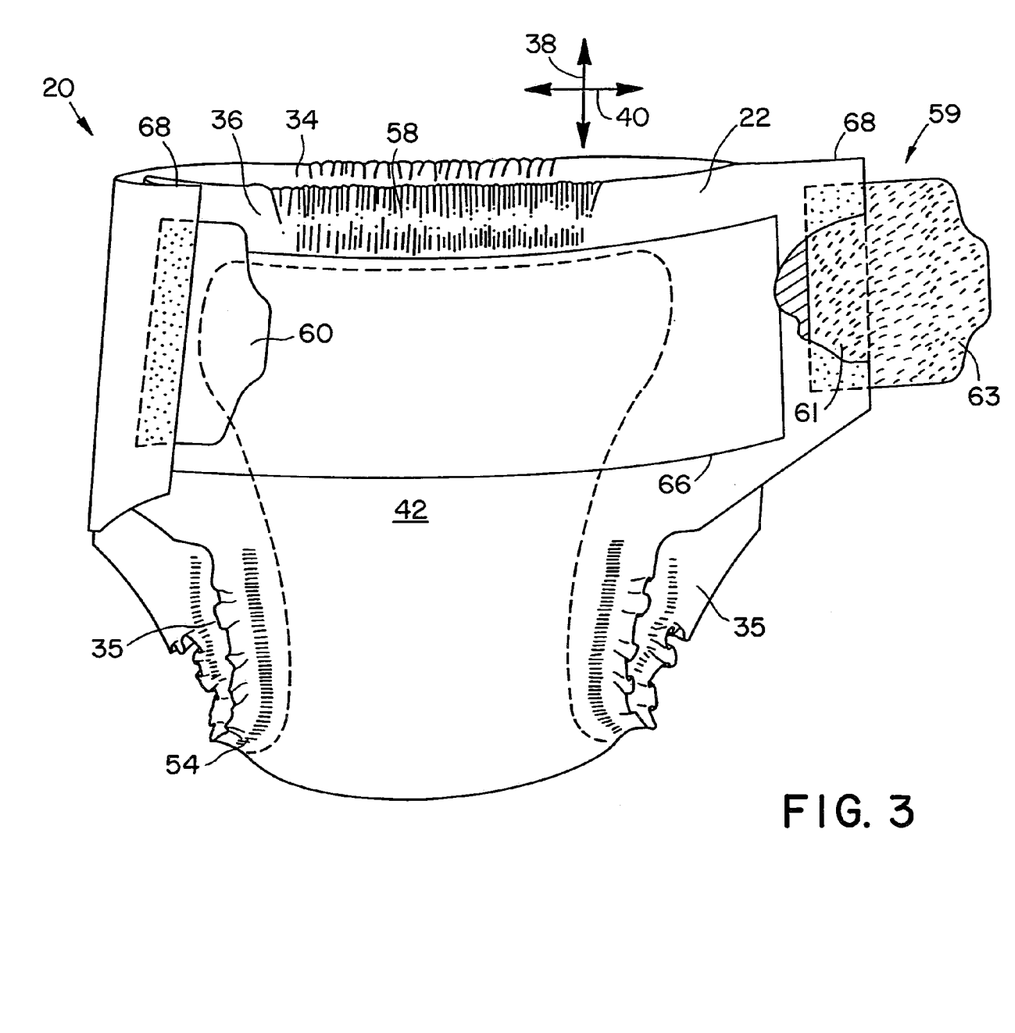
FIG. 3 representatively shows a front plan view of the pant-like prefastened, disposable absorbent article of FIG. 1 with a waist size adjustment means in an unengaged position, and with portions of the article partially cut away to show the underlying features, according to one embodiment of this invention.
Figure 4:
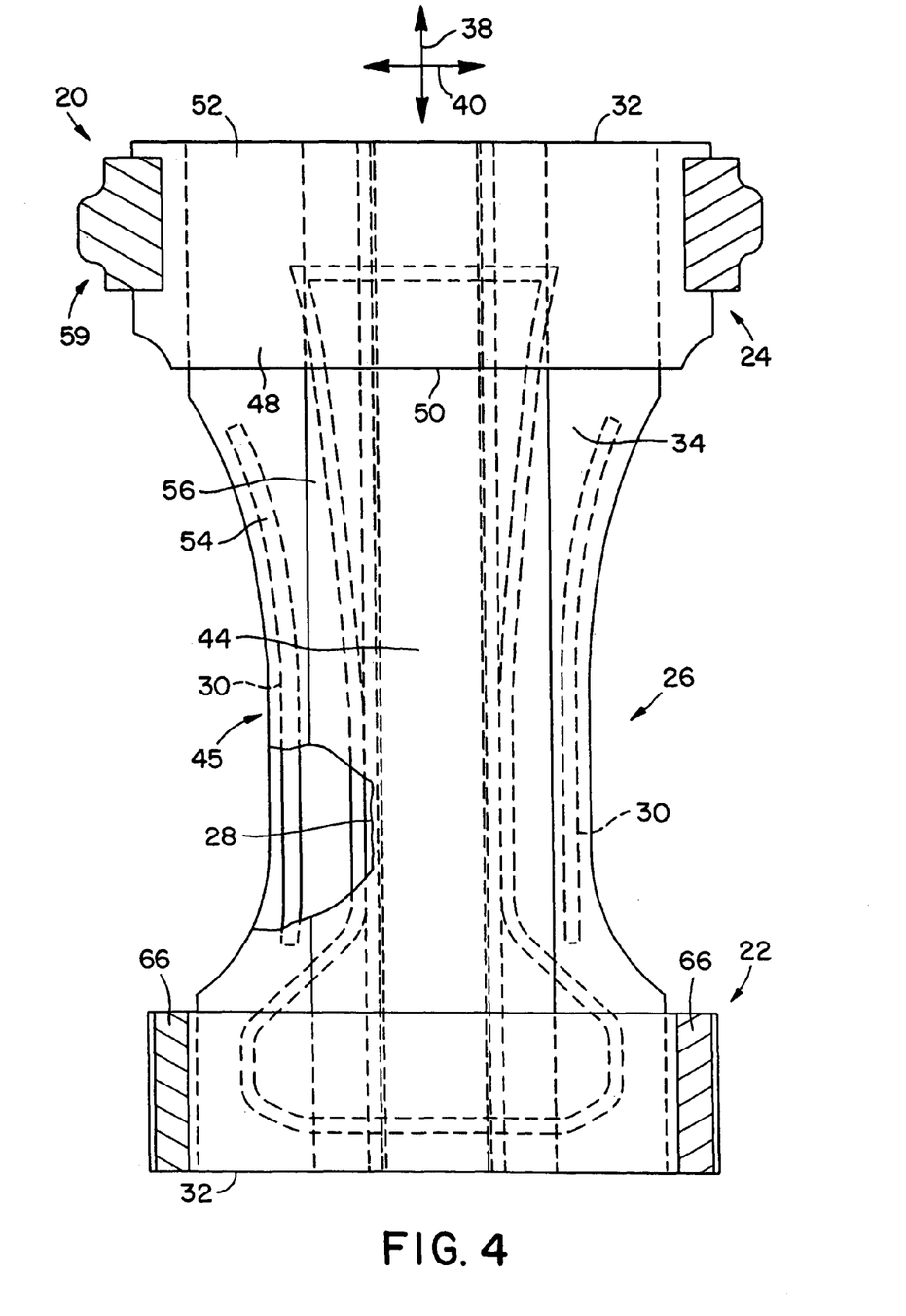
FIG. 4 representatively shows a plan view of the pant-like prefastened, disposable absorbent article of FIG. 1 in an unfastened, stretched and laid flat condition with a surface of the article which contacts the wearer's skin facing the viewer, and with a portion of the article partially cut away to show the underlying features, according to one embodiment of this invention.
Figure 5:
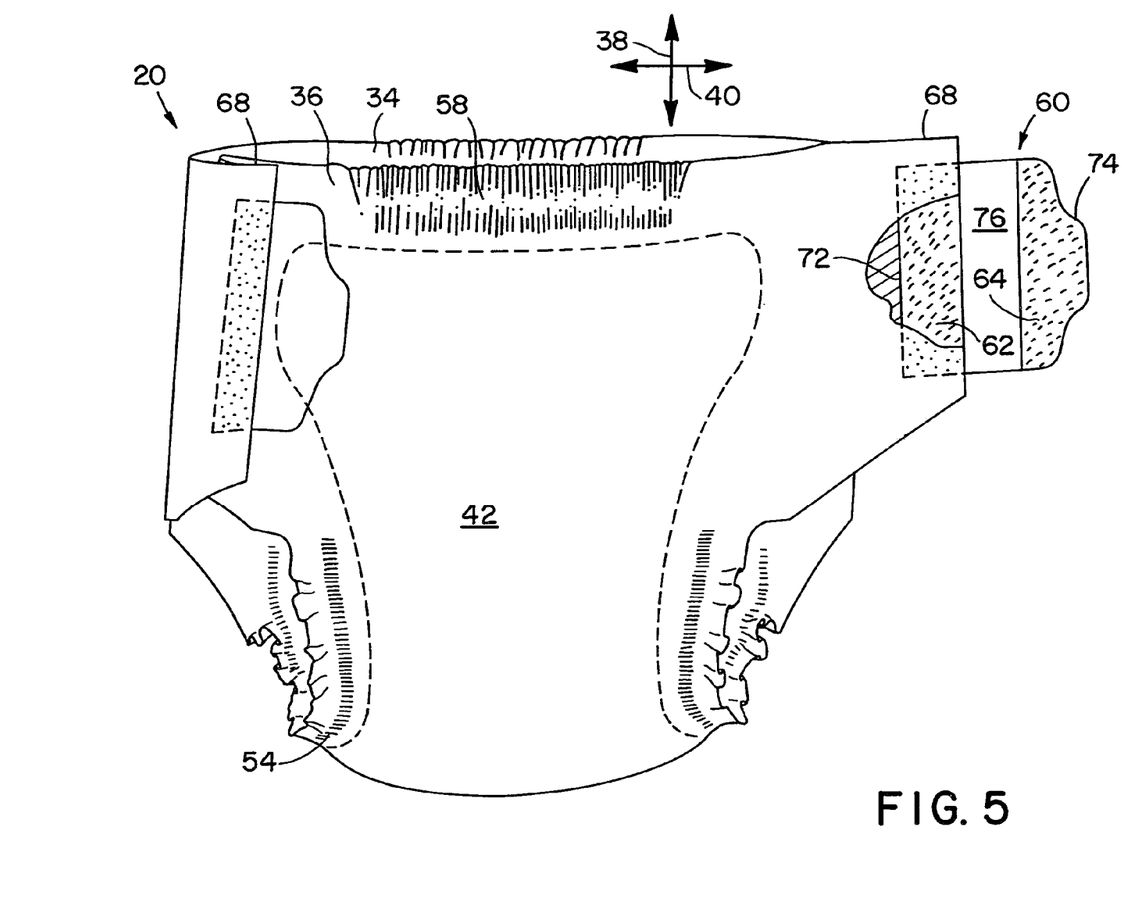
FIG. 5 representatively shows a front plan view of a pant-like prefastened, disposable absorbent article having a waist size adjustment means in an unengaged position, and with portions of the article partially cut away to show the underlying features, according to one embodiment of this invention.

Referring to FIGS. 1-6, a pant-like prefastened, disposable diaper 20 of the present invention defines a front waist region 22, a back waist region 24, and a crotch region 26 that extends between and connects the front waist region 22 and the back waist region 24. For reference, arrows 38 and 40 depicting the orientation of the longitudinal axis and the lateral axis, respectively, of the diaper 20 are illustrated in FIGS. 3-5.

As shown in FIG. 4, the front waist region 22 includes the portion of the diaper 20 that, when worn, is positioned on the front of the wearer while the back waist region 24 includes the portion of the diaper 20 that, when worn, is positioned on the back of the wearer. The crotch region 26 of the diaper 20 includes the portion of the diaper 20 that, when worn, is positioned between the legs of the wearer and covers the lower torso of the wearer.

The diaper 20 defines a pair of laterally opposing side edges 30, a pair of longitudinally opposing waist edges 32, an interior surface 34 that is configured to contact the wearer, and an exterior surface 36 opposite the interior surface 34 that is configured to contact the wearer's clothing during use. As shown in FIGS. 1-5, the diaper 20 also includes an outer cover 42 and a bodyside liner 44 that is connected to the outer cover 42 in a superposed relation. An absorbent core 28 is located between the outer cover 42 and the bodyside liner 44. The outer cover 42, the bodyside liner 44 and the absorbent core 28 define a chassis 45 of the diaper 20, which forms the waist opening 33 and each leg opening 35. The laterally opposing side edges 30 are generally defined by the side edges of the outer cover 42 that further define leg openings 35, which desirably are curvilinear. The waist edges 32 are generally defined by the waist edges of the outer cover 42 and form the waist opening 33 that is configured to encircle the waist of the wearer during use. In one embodiment of this invention, a portion of the chassis 45 positioned about or forming a periphery of the waist opening 33 has an elastic tension of about 100 grams to about 1400 grams. The absorbent core 28 is configured to contain and/or absorb any body exudates discharged from the wearer.

In accordance with one embodiment of this invention, the chassis 45 is relatively narrow in the crotch region 26 to allow the wearer to step directly into and through each leg opening 35. Desirably, a width of the chassis 45 at the crotch region 26 is less than the relaxed waist opening measurement. Generally, the width of the chassis 45 which defines a "crotch elastic spacing" is a measurement of the lateral distance between the outside edges 30 of the leg elastic members in the crotch region of the chassis 45, measured at the narrowest point or spacing of the leg elastic members in the crotch region of the chassis 45 along the longitudinal axis 38. In accordance with one embodiment of this invention, the absorbent core 28 has a width at the crotch region 26 desirably of less than about 5.0 inches, for a step 4 diaper, in order that the width of the chassis 45 at the crotch region 26 is less than the relaxed waist opening diameter. It is apparent that the width at the crotch region 26 must vary proportionally for diapers having different step sizes. Generally, the width of the absorbent core 28 is a measurement of the lateral distance between opposing side edges of the absorbent core 28 at the narrowest point of the absorbent core 28 along the longitudinal axis 38. For comparison, if the width of the chassis 45 at the crotch region 26 is greater than the relaxed waist opening diameter, the wearer will not be able to step into and through the leg opening 35 and application of the diaper 20 in a manner similar to a conventional training pant is difficult.

The diaper 20 may be of various suitable shapes. For example, in the unfastened configuration as shown in FIG. 4, the diaper 20 may have an overall rectangular shape, T-shape or an approximate hourglass shape. In the shown embodiment, the diaper 20 has a generally I-shape in an unfastened configuration. Examples of suitable diaper configurations and suitable diaper components are described in U.S. Pat. No. 4,798,603, issued Jan. 17, 1989 to Meyer et al.; U.S. Pat. No. 5,176,668, issued Jan. 5, 1993 to Bernardin; U.S. Pat. No. 5,176,672, issued Jan. 5, 1993 to Bruemmer et al.; U.S. Pat. No. 5,192,606, issued Mar. 9, 1993 to Proxmire et al.; and U.S. Pat. No. 5,509,915, issued Apr. 23, 1996 to Hanson et al., the disclosures of which are hereby incorporated by reference. The various components and configurations of the diaper 20 according to embodiments of this invention provide a desired fit range, as well as softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic, and thermal bonds, and combinations thereof. In the shown embodiment, for example, the outer cover 42 and bodyside liner 44 are assembled to each other and to the absorbent core 28 with an adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, the other components of the diaper 20 may be assembled into the diaper 20 by employing the above-identified attachment mechanisms.

In accordance with one embodiment of this invention, as shown in FIGS. 1-6, the outer cover 42 is extensible, for example as described in U.S. patent application Ser. No. 09/563,417 filed on May 3, 2000 by Roessler et al. The disclosure of application Ser. No. 09/563,417 is incorporated herein by reference to the extent it assists the present disclosure. The outer cover 42 of the diaper 20, as shown in FIGS. 1-4, may suitably be composed of a material which is either water vapor permeable or water vapor impermeable. It is generally desired that the outer cover 42 be formed from a material that is substantially impermeable to liquids and permeable (breathable) to water vapor. The outer cover 42 can be manufactured from a thin plastic film or other suitable flexible liquid-impermeable material. For example, the outer cover 42 may be formed from a polyethylene film having a thickness of about 0.013 millimeter (0.5 mil) to about 0.051 millimeter (2.0 mils). If a more clothlike feeling is desired, the outer cover 42 may be formed from a polyolefin film having a nonwoven web, such as a spunbond web of polyolefin fibers, laminated to an exterior surface thereof. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868, issued to McCormack et al.; and U.S. Pat. No. 5,843,056, issued Dec. 1, 1998 to Good et al., the disclosures of which are hereby incorporated by reference. Still further, the outer cover 42 may also be an elastomeric material such as a stretch-thermal laminate (STL), a neck-bonded laminate (NBL), or a stretch-bonded laminate (SBL) material. Methods of making such materials are well known to those skilled in the art and are described in U.S. Pat. No. 4,663,220, issued May 5, 1987 to Wisneski et al.; U.S. Pat. No. 5,226,992, issued Jul. 13, 1993 to Mormon; and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

As shown in FIG. 4, the bodyside liner 44 suitably presents a bodyfacing surface that is compliant, soft feeling, and non-irritating to the wearer's skin. In accordance with one embodiment of this invention, the bodyside liner 44 is desirably made of an elastic and/or an extensible material. For example, the bodyside liner 44 may be made from extensible materials as are described in U.S. patent application Ser. No. 09/563,417 filed on May 3, 2000 by Roessler et al. Desirably, these materials are elastic or extensible in at least a lateral direction, parallel to the lateral axis depicted by arrow 40 in FIG. 4.

Further, the bodyside liner 44 may be less hydrophilic than the absorbent core 28 to present a relatively dry surface to the wearer and may be sufficiently porous to be liquid permeable, permitting liquid to readily penetrate through its thickness. Suitable web materials for manufacturing the bodyside liner 44 include, but are not limited to, porous foams, reticulated foams, apertured plastic films, natural fibers (for example, wood or cotton fibers), synthetic fibers (for example, polyester or polypropylene fibers), and/or a combination of natural and synthetic fibers. The bodyside liner 44 is suitably employed to help isolate the wearer's skin from liquids held in the absorbent core 28.

Various woven and nonwoven fabrics can be used for the bodyside liner 44. For example, the bodyside liner 44 may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In one embodiment of the invention, the bodyside liner 44 is made from a nonwoven, spunbond, polypropylene fabric composed of about 2.8 to about 3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin.

The absorbent core 28 of the diaper 20 may suitably be composed of a matrix of hydrophilic fibers, such as a web of cellulosic fluff, mixed with particles of a high-absorbency material commonly known as superabsorbent material. In one embodiment of this invention, the absorbent core 28 includes a matrix of cellulosic fluff such as wood pulp fluff and superabsorbent hydrogel-forming particles. The wood pulp fluff may be exchanged with synthetic, polymeric, meltblown fibers, or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 28 to better contain and absorb body exudates. The concentration of the superabsorbent particles may also vary through the thickness of the absorbent core 28. Alternatively, the absorbent core 28 may comprise a laminate of fibrous webs and superabsorbent material or other suitable means of maintaining a superabsorbent material in a localized area.

The absorbent core 28 may have any suitable shape. For example, the absorbent core 28 may be rectangular, I-shaped, or T-shaped. Desirably as discussed above, the absorbent core 28 is narrow in the crotch region 26 of the diaper 20. The width of the absorbent core 28 in the crotch region 26 desirably is about 2.5 centimeters to about 12.7 centimeters (1.0 inch to about 5.0 inches), more desirably not greater than about 7.6 centimeters (3.0 inches) and even more desirably not greater than about 5.1 centimeters (2.0 inches). The narrow width of the absorbent core 28 in the crotch region 26 allows the absorbent core 28 to better fit between the legs of the wearer. In accordance with one embodiment of this invention, the chassis material which extends beyond the edges of the absorbent core 28 is gathered to maintain the relative width of the chassis 45 in the crotch region 26 with respect to the relaxed waist opening diameter. Suitable methods of gathering the chassis material, for example by using elastic materials, are well known to those having skill in the art. It is apparent that the dimensions and the absorbent capacity of the absorbent core 28 should properly correspond to the size of the intended wearer and the liquid loading imparted by the intended use of the diaper 20.

Suitable high-absorbency materials for the absorbent core 28 include, but are not limited to, natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of suitable synthetic, polymeric, high-absorbency materials include, but are not limited to, the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 28 include, but are not limited to, natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and similar compounds. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. Generally, it is desired that the high absorbency material be in the form of discrete particles. However, the high absorbency material may also be in the form of fibers, flakes, rods, spheres, needles, or the like. Generally, the high absorbency material is present in the absorbent core 28 in an amount of about 5 weight percent to about 90 weight percent, based on a total weight of the absorbent core 28.

In accordance with one embodiment of this invention, a substantially hydrophilic tissue wrapsheet (not shown) may be employed to help maintain the integrity of the airlaid fibrous structure of the absorbent core 28. The tissue wrapsheet is typically placed about the absorbent core 28 over at least one of the major facing surfaces thereof and composed of an absorbent cellulosic material, such as creped wadding or a high wet-strength tissue. In accordance with one embodiment of the invention, the tissue wrapsheet can be configured to provide a wicking layer that helps to rapidly distribute liquid over the mass of absorbent fibers comprising the absorbent core 28. The tissue wrapsheet on one side of the absorbent fibrous mass may be bonded to the tissue wrapsheet located on the opposite side of the fibrous mass to effectively entrap the absorbent core 28. In accordance with one embodiment of this invention, the tissue wrap sheet may be necked, pleated and/or have any suitable design known to those having ordinary skill in the art to extend in at least one direction, for example the lateral or cross-machine direction, without tearing or ripping.

In accordance with one embodiment of this invention as shown in FIGS. 1 and 4, the diaper 20 includes a pair of containment flaps 56 that are configured to provide a barrier to the lateral flow of body exudates. The containment flaps 56 may be located along the laterally opposing side edges 30 of the diaper 20 adjacent the side edges of the absorbent core 28. Each containment flap 56 typically defines an unattached edge that is configured to maintain an upright, perpendicular configuration in at least the crotch region 26 of the diaper 20 to form a seal against the wearer's body. Each containment flap) 56 extends longitudinally along at least a portion of a length of the absorbent core 28. Desirably, each containment flap 56 extends along substantially the entire length of the absorbent core 28 to better contain the body exudates. In accordance with one embodiment of this invention wherein each containment flap 56 extends along a portion of the length of the absorbent core 28, the containment flaps 56 can be selectively positioned along the side edges 30 of the diaper 20 in the crotch region 26. Such containment flaps 56 are generally well known to those skilled in the art. For example, suitable constructions and arrangements for containment flaps 56 are described in U.S. Pat. No. 4,704,96, issued Nov. 3, 1987 to K. Enloe, the disclosure of which is hereby incorporated by reference.

In accordance with one embodiment of this invention, each containment flap 56 may be necked, mechanically sectioned and/or tacked down in a limited area to allow the bodyside liner 44 and the outer cover 42 to extend so that the waist opening 33 of the diaper 20 is adjustable. Thus, the fit range of the diaper 20 is not negatively affected by the use of the containment flaps 56 in the diaper 20.

In accordance with one embodiment of this invention, at least a portion of the waist edges 32 and the side edges 30 are elastic or extensible to improve the fit range of the diaper 20 and support the absorbent core 28 to prevent leakage of body exudates. For example, as shown in FIGS. 1-5, the diaper 20 may include a pair of leg elastic members 54 that are connected to the laterally opposing side edges 30 of the diaper 20 in the crotch region 26. The diaper 20 may also include a pair of waist elastic members 58 that are connected to the longitudinally opposing waist edges 32 of the diaper 20. The leg elastic members 54 and the waist elastic members 58 are generally adapted to fit about the legs and waist of a wearer, respectively, to maintain a positive, contacting relationship with the wearer to effectively reduce or eliminate the leakage of body exudates from the diaper 20.

Materials suitable for use as the leg elastic members 54 and the waist elastic members 58 are well known to those skilled in the art. For example, sheets, filaments, strands or ribbons of a polymeric, elastomeric material may be adhered to the outer cover 42 in a stretched position or attached to the outer cover 42 while the outer cover 42 is pleated, such that elastic constrictive forces are imparted to the outer cover 42. The leg elastic members 54 may also include such materials as polyurethane, synthetic rubber and natural rubber.

In accordance with one embodiment of this invention as shown in FIG. 4, the diaper 20 includes a fit panel 48 superimposed adjacent to the waist edge 32 in at least one of the front waist region 22 and the back waist region 24 to provide a more comfortable, contouring fit about the wearer. Desirably, the fit panel 48 is elastic, elastomeric or extensible in at least one direction, such as the cross-machine or lateral direction. For example, as shown in FIG. 4, the diaper 20 includes an elastomeric fit panel 48 on the interior surface 34 of the diaper 20 that is configured to elongate in the lateral direction to provide an improved fit range and enhanced appearance of the diaper 20. Desirably, the elastic or extensible fit panel 48 allows the waist opening 33 to be adjusted, thereby increasing the extended waist opening measurement to assist in applying the diaper 20 onto the wearer. The fit panel 48 is also configured with respect to the diaper 20 such that the absorbent core 28 has the ability to move and receive body exudates without adversely affecting the positioning of the fit panel 48 and the diaper 20 about the waist of the wearer. Thus, movements of the wearer may cause the absorbent core 28 to move but do not adversely affect the overall positioning and fit of the diaper 20 on the wearer. Such improved fit can result in reduced leakage from the diaper 20, increased comfort, and a more aesthetically pleasing appearance.

As shown in FIG. 4, in accordance with one embodiment of this invention, the fit panel 48 is located on the interior surface 34 and extends longitudinally beyond the side edges of the absorbent core 28 so that the fit panel 48 is generally coterminous with the waist edge 32 in the respective front waist region 22 and/or back waist region 24. When located on the interior surface 34 of the diaper 20, the fit panel 48 may define a free edge 50 that extends longitudinally inward towards the crotch region 26 of the diaper 20. In accordance with one embodiment of this invention, the free edge 50 is configured to remain at least partially unattached to the bodyside liner 44 to allow the absorbent core 28 to move, for example expand, to receive and contain body exudates. The unattached free edge 50 allows a pocket to form between the fit panel 48 and the bodyside liner 44 to contain body exudates. Further, the free edge 50, as well as the waist edge 52 of the fit panel 48, may be linear or curvilinear to better fit the wearer. Desirably, if the free edge 50 is curvilinear, the waist edge 52 is also curvilinear to improve the manufacturing process and reduce manufacturing waste.

Suitable materials for producing the fit panel 48 include, but are not limited to, stretch-bonded-laminate (SBL) materials, neck-bonded-laminate (NBL) materials, elastomeric films, elastomeric foam materials, and/or the like. For example, suitable meltblown elastomeric fibrous webs are described in U.S. Pat. No. 4,663,220, issued May 5, 1987 to T. Wisneski et al., the disclosure of which has previously been incorporated by reference. Examples of suitable composite fabrics comprising at least one layer of a nonwoven material secured to a fibrous elastic layer are described in European Patent Application No. EP 090 010 published on Apr. 8, 1987 with the inventors listed as J. Taylor et al., the disclosure of which has previously been incorporated by reference. Examples of suitable NBL materials are described in U.S. Pat. No. 5,226,992, issued Jul. 13, 1993 to Morman, the disclosure of which has previously been incorporated by reference.

In accordance with one embodiment of this invention, the fit panel 48 may be attached to the diaper 20 in any suitable manner that provides the desired elastic or extensible properties. For example, the fit panel 48 may be attached to the diaper 20 using adhesive, ultrasonic, and/or thermal bonding techniques, and the like.

As shown in FIGS. 1-4, in accordance with one embodiment of this invention, the diaper 20 includes a fastening system 59 having at least one, and desirably two laterally opposing refastenable, prefastened fasteners 60. The fasteners 60 are permanently bonded, adhered or otherwise attached directly or indirectly to the diaper 20 at or laterally inward from its side edges 30, in one of the front waist region 22 or the back waist region 24. The fasteners 60 may be permanently bonded or attached in the vicinity of the side edges 30 of the diaper 20 by any means known to those skilled in the art such as adhesive bonds, sonic bonds or thermal bonds. Desirably, the fasteners 60 are permanently bonded or attached to the back waist region 24, having the extensible fit panel 48, using bonds having a width of less than about 0.5 inch. Alternatively, the fasteners 60 may be permanently bonded or attached directly to the extensible fit panel 48. Attaching the fasteners 60 onto the front waist region 22 or the back waist region 24 that the extensible fit panel 48 is attached to, or directly to the extensible flit panel 48, provides added fit, flexibility, and an optimum seal in the corresponding front waist region 22 or the back waist region 24 once the diaper 20 is positioned on the wearer.

As shown in FIG. 3, in accordance with one embodiment of this invention, at least one of the fasteners 60 may include a unitary, continuous fastening segment having a first engageable portion 61 that provides a prefastened, refastenable side seam 68 and a second engageable, portion 63 that provides a waist size adjustment means. The second engaging portion 63 is refastenably engageable with an attachment panel 66 and/or the exterior surface 36 of the diaper, independently of the refastenable side seam 68, whereby a waist perimeter dimension can be adjusted to conform to the waist of the wearer, as discussed below. When the first engageable portion 61 of each fastener 60 is refastenably engaged with the corresponding front waist region 22 and/or back waist region 24, providing the prefastened refastenable side seams 68, the laterally opposing side edges 30 of the diaper 20 each defines a leg opening 35 which is configured to encircle a leg of the wearer. Further, the waist edges 32 define the waist opening 33. The second engageable portion 63 of each fastener 60 is refastenably engageable, directly with the outer surface 36 or alternatively with an attachment panel 66 which extends laterally across the outer surface 36 of the front waist region 22, as shown in FIGS. 1-3. The use of the fasteners 60 that provides both the side seam 68 and a waist size adjustment means with one continuous fastening segment advantageously simplifies the manufacturing process and reduces raw material requirements, resulting in reduced manufacturing costs.

In accordance with one embodiment of this invention as shown in FIGS. 1-3, an extensible or elastic attachment panel 66 may include a single piece of material, such as a loop component material, that extends substantially across the respective waist region of the diaper 20. In this configuration, the attachment panel 66 located on the outer cover 42 may further extend beyond the side edges 30 of the diaper 20 and include a folded over portion to which the first engageable portion 61 of continuous fastener 60 is refastenably engaged to provide the prefastened refastenable side seams 68.

Desirably, the second engageable portion 63 is made of a suitable releasably engageable fastener, such as an adhesive tape tab fastener, hook fastener, loop fastener, mushroom fastener, snap, pin, belt and the like, and combinations thereof. For example, as shown in FIG. 3, the second engageable portion 63 may include a plurality of hook type fasteners and the attachment panel 66 and/or the outer cover 42 may be configured to function as a complimentary loop type fastener.

As shown in FIG. 4, in accordance with one embodiment of this invention, the diaper 20 includes two separate attachment panels 66 located along the opposing side edges 30 on the interior surface 34 in the front waist region 22. The first engageable portion 61 of each fastener 60, which are permanently bonded or attached to the diaper 20 in the opposing waist region, for example the back waist region 24, are releasably engaged to the attachment panels 66 to provide the prefastened, refastenable side seams 68. Alternatively, if the fasteners 60 are located on the front waist region 22, the attachment panels 66 may be located along the interior surface 34 of the diaper 20 in the back waist region 24. The attachment panels 66 may be otherwise located on the exterior surface 36 of the diaper 20 at the front waist region 22 and/or the back waist region 24, depending upon the location of the fasteners 60. In such configurations, the prefastened, refastenable side seams 68 may be formed as described above, provided that the interior surface 34 or the exterior surface 36 of the diaper 20 to which the attachment panels 66 are attached, are configured to be exposed to the first engageable portions 61 of the fastener 60.

Desirably, the side seams 68 are configured such that the exterior surface 36 of the front waist region 22 is refastenably attached to the interior surface 34 of the back waist region 24. As such, multiple benefits are realized. For example, the longitudinally inward folded portion of the front waist region 22 ensures that none of the side seam 68 and the fastener 60 is exposed to the wearer's skin, reducing undesirable skin irritation. Moreover, in such a configuration, the fastener 60 is subjected to shear forces in use, such that the diaper 20 is more securely fastened upon the wearer. Finally, the fasteners 60, permanently bonded or attached to the back waist region 24 of the diaper 20, refastenably engage the diaper 20 in the front waist region 22 increasing the ease with which the wearer or the caregiver can adjust the fit of the diaper 20.

The waist size adjustment means provides improved fit and securement of the diaper 20 about the waist of the wearer after the diaper 20 has been placed on the wearer in the prefastened configuration or state. The waist size adjustment means is configured to reduce the waist perimeter dimension of the waist opening 33 to further conform the waist opening 33 to the waist of the wearer after initial donning of the diaper 20. The waist perimeter dimension is a peripheral or circumferential measurement of the waist opening 33, which should generally correspond to the waist of the wearer during use of the diaper 20. Referring to FIGS. 1 and 3, the second engageable portion 63 of the continuous fastener 60 extends from the prefastened, refastenable side seam 68 and is desirably configured to refastenably engage the attachment panel 66 and/or the exterior surface 36 of the front waist region 22. Alternatively, the second engageable portion 63 of the continuous fastener 60 may be configured to refastenably engage the exterior surface 36 of the back waist region 24.

Desirably, but not necessarily, the laterally opposing fasteners 60 are prefastened to the attachment panel 66 at least about 1.0 inch apart during the manufacturing process. With the laterally opposing fasteners 60 positioned at least about 1.0 inch apart, the initial donning of the diaper 20 is made possible without the need to unfasten the fasteners 60. In such a configuration, the prefastened diaper 20 can be pulled on and/or off over the legs and hips of the wearer, similar to conventional training pants. In accordance with one embodiment of this invention, the fasteners 60 may be prefastened to the attachment panel 66 at a distance greater than 1.0 inch apart to allow for a larger relaxed waist opening measurement for easier application of the diaper 20.

After the initial donning of the diaper 20, at least one of the refastenable fasteners 60 provides the waist size adjustment means for adjusting the waist perimeter dimension of the waist opening 33, as shown in FIG. 1. With the diaper 20 positioned about the waist of the wearer, the waist perimeter dimension may be adjusted by unfastening at least one of the fasteners 60 from the attachment panel 66 and refastening the at least one fastener 60 at a lateral position along the attachment panel 66 to either reduce or increase the waist perimeter dimension corresponding to the waist opening 33.

The prefastened, refastenable side seams 68 can also be easily disengaged to inspect the diaper 20 for possible soiling or to first apply the diaper 20 to the wearer if desired. If the prefastened diaper 20 becomes soiled during use, the prefastened, refastenable side seams 68 can be disengaged to easily remove the diaper 20 in a similar manner as conventional diaper articles.

In accordance with one embodiment of this invention, the prefastened, refastenable side seams 68 on the diaper 20 may further include passive bonds 70 (which, themselves, are not refastenable) for maintaining the diaper 20 in the prefastened condition, particularly when it is being pulled over the hips of the wearer. Desirably, the passive bonds 70 are easily broken or destroyed to release or disconnect the front waist region 22 from the back waist region 24. Absorbent articles including such passive bonds 70 and methods of making the passive bonds 70 are further described in U.S. Pat. No. 6,287,287, issued Sep. 11, 2001 to Elsberg on Jun. 19, 1998 and U.S. Pat. No. 6,036,805 issued Mar. 14, 2000 to McNichols, the disclosures of which are hereby incorporated by reference.

For example, as shown in FIGS. 1-2, the side seams 68 of the diaper 20 may include passive bonds 70 that releasably connect the side edges of the back waist region 24 to the front waist region 22 of the diaper 20. The passive bonds 70 assist in securing the refastenable side seams 68, that prevent movement and shifting of the side edges 30 of the front waist region 22 and the back waist region 24, relative to each other for improved fit and performance. The passive bonds 70 also provide improved hip coverage and prevent rollover or folding of the side edges 30 and the waist edges 32 of the prefastened diaper 20 as the prefastened diaper 20 is pulled over the wearer's hips. Such prevention of rollovers and folding can reduce the level of contact between the fasteners 60 and the skin of the wearer, thus, resulting in reduced skin irritation and redness.

The passive bonds 70 may be located on the diaper 20 in any manner that provides the desired improved fastening while maintaining the desired elastic or extensible properties of the diaper components being bonded. For example, as shown in FIGS. 1 and 2, the passive bonds 70 may be located laterally inward of the side edges 30 of the front waist region 22 and/or the back waist region 24, adjacent to or included with the refastenable side seams 68. In such a configuration, the passive bonds 70 connect the front waist region 22 to the back waist region 24 of the diaper 20 in a facing relationship.

The passive bonds 70 can be provided by any type of bonding well known to those skilled in the art, such as thermal, adhesive and ultrasonic bonding, and may be discrete point bonds, dashed lines, continuous lines, discontinuous lines and the like, or combinations thereof. Desirably, as shown in FIG. 6, the passive bonds 70 form a zig zag bond pattern 104. In accordance with one embodiment of this invention, the zig zag bond pattern 104 allows lateral side panels 106 to elongate or expand around a wearer's waist without the passive bonds 70 opening or "zippering" from the stress of application. Desirably, each side panel 106 is elastic or extensible in at least one direction, for example the cross-machine direction. The zig zag bond pattern 104 has greater strength in the cross-machine direction (shear) than in the machine direction (peel) in order to provide an easy opening joint if it is desired that the diaper 20 be opened along the side seams 30 for application or removal as a conventional diaper article. Desirably, the passive bonds 70 are ultrasonic point bonds, which can be destroyed upon the first opening of the diaper 20. Moreover, the passive bonds 70 may have any suitable shape such as circular, square, triangular and the like.

In accordance with one embodiment of this invention as shown in FIG. 5, each fastener 60 may include a primary fastener 62 and a waist size adjustment means, for example a secondary fastener 64. The primary fastener 62 may be permanently bonded or attached to the side edge 30 in one of the front waist region 22 and the back waist region 24 and refastenably attached to the side edge 30 in the opposite waist region 22 or 24 to provide the refastenable side seams 68.

The secondary fasteners 64 extend from the refastenable side seams 68 to form the waist size adjustment means. The secondary fasteners 64 are configured to encircle the hips of the wearer and engage the exterior surface 36 of the front waist region 22 of the diaper 20 or alternatively, the attachment panel 66, to reduce the waist perimeter dimension of the waist opening 33 and conform the waist opening 33 to the wearer's waist. It is apparent that the secondary fasteners 64 may alternatively be located on the front waist region 22 and may be configured to releasably engage the exterior surface 36 of the back waist region 24. Alternatively, the diaper 20 may include a single secondary fastener 64 extending from one of the refastenable side seams 68.

As shown in FIG. 5, the fasteners 60, when configured with multiple engaging portions, may include an intermediate portion 76 between the primary fastener 62 and the secondary 64 fastener. For instance, when the fasteners 60 include hook-type fastener elements in the multiple engaging portions, the intermediate portion may be devoid of hook-type fastening elements. Desirably, the intermediate portion 76 is made of an elastic or extensible material. Thus, the intermediate portion 76 provides improved fit and comfort to the wearer by allowing the fastener 60 more flexibility and range in engaging the attachment panel 66 and/or the exterior surface 36 of the diaper 20, either or both of which may include a loop fastening material. Suitable materials for the intermediate portion 76 include, but are not limited to, stretch-bonded-laminate (SBL) materials, neck-bonded-laminate (NBL) materials, elastomeric films, elastomeric foam materials, laminates of nonwoven webs with elastomeric strands, filaments or films, and the like, such as described above as being suitable for the fit panel 48.

In accordance with one embodiment of this invention, the intermediate portion 76 of the fastener 60 may include a hinge to which the primary fastener 62 and the secondary fastener 64 are attached. When the intermediate portion 76 is configured as a hinge, the fastener 60 desirably is thinner at the intermediate portion 76, and therefore more flexible for easier attachment of the secondary fastener 64 to the attachment panel 66 and/or the exterior surface 36 of the diaper 20.

The prefastened, refastenable side seams 68, which may include passive bonds 70, are configured to maintain the diaper 20 in a prefastened configuration as it is pulled on and off over the hips of the wearer during use. Thus, it is desirable that the prefastened refastenable side seams 68 provide adequate strength to maintain the front ears aligned without twisting or folding while donning. Such strengths are well known to those skilled in the art. Similarly, the waist size adjustment means, which may include the second engageable portion 63 of the continuous fastener 60 or the secondary fastener 64, should provide adequate shear strength and peel strength to maintain engagement with the exterior surface 36 of the diaper 20 during donning and use.

The side seams 68 are also configured to be readily broken such that the caregiver can easily peel the fastener 60 from the front waist region 22 or the back waist region 24 to remove the diaper 20 from the wearer after it has been soiled, to inspect the diaper for soiling or to initially position the diaper 20 on the wearer if desired. Thus, it is desirable that the side seams 68 define a relatively low peel strength such that the caregiver can readily disengage the side seams 68 and break the passive bonds 70 to separate the front waist region 22 and the back waist region 24 to remove the diaper 20 from the waist of the wearer similar to conventional diapers that are not prefastened. These features of the side seams 68 contribute to the convertibility of the article. Similarly, the waist size adjustment means that may include the second engageable portion 63 of the fastener 60 or the secondary fastener 64, are also configured to be readily broken such that the caregiver or the wearer can disengage the waist size adjustment means from the exterior surface 36 of the diaper 20 by peeling the fastener 60 from the attachment panel 66. This allows for the repositioning of the diaper 20 about the hips of the wearer or for inspection of the diaper 20. Thus, it is desirable that the waist size adjustment means define a relatively low peel strength such that the caregiver can readily disengage the waist size adjustment means from the exterior surface 36 of the diaper 20. Suitable peel strength values are well known to those skilled in the art. One test for measuring peel strength of hook and loop fasteners is ASTM D1876-72. This test is described in U.S. Pat. No. 5,176,671, issued to Roessler et al., the disclosure of which is incorporated herein by reference.

EXAMPLE 1

As shown in FIG. 7, a pant-like prefastened, disposable absorbent article of the present invention has two leg openings 35 which are positioned directly below and visible through the waist opening 33. The crotch elastic spacing is less than a relaxed waist opening diameter 90. Thus, a wearer is able to directly place his or her foot into and through each leg opening 35 to easily apply the absorbent article. The fasteners 60 are in the prefastened configuration and separated by a distance to provide the desired relaxed waist opening diameter 90. Desirably, the fasteners 60 are separated by a lateral spacing of at least about 25 mm, more desirably at least about 50 mm and still more desirably at least about 100 mm. As shown in FIG. 7, a generally circular cylindrical rod 94 having a diameter of about 0.635 cm (0.25 inch) can be vertically inserted, parallel to the vertical axis 92 of the absorbent article, into and the through the waist opening 33 and one leg opening 35 without touching the leg elastic member 54 of the leg opening 35. Thus, in a prefastened configuration, a first side panel 106 extends in a direction away from the vertical axis 92 a distance 200, as shown in FIG. 7, at least about 0.635 cm (0.25 inch) beyond the leg elastic member 54 in the crotch region 26. Desirably, a laterally opposing second side panel 106 extends at least about 0.635 cm (0.25 inch) beyond the laterally opposing leg elastic member 54 in the crotch region. Thus, for example, the relaxed waist opening diameter 90 will be at least about 0.50 inch (0.127 cm) greater than the crotch elastic spacing.

EXAMPLE 2

Six samples (Samples 1-6) of an absorbent article of the present invention, each having two prefastened fasteners positioned or spaced apart from each other at varying lateral distances along the attachment panel, were compared to four samples of conventional absorbent articles (Samples 7-10).

Sample 1 is an absorbent article produced according to the present invention, having a spacing of about 2.0 inches between the prefastened fasteners along the attachment panel.

Sample 2 is an absorbent article produced according to the present invention, having a spacing of about 2.5 inches between the prefastened fasteners along the attachment panel.

Sample 3 is an absorbent article produced according to the present invention, having a spacing of about 3.0 inches between the prefastened fasteners along the attachment panel.

Sample 4 is an absorbent article produced according to the present invention, having a spacing of about 3.5 inches between the prefastened fasteners along the attachment panel.

Sample 5 is an absorbent article produced according to the present invention, having a spacing of about 4.0 inches between the prefastened fasteners along the attachment panel.

Sample 6 is an absorbent article produced according to the present invention, having a spacing of about 5.0 inches between the prefastened fasteners along the attachment panel.

Sample 7 is an absorbent article produced by Kimberly-Clark Corporation under the tradename PRIVATE LABEL Pull-on.

Sample 8 is an absorbent article produced by Proctor and Gamble Corporation under the tradename EASY UPS Pull-on.

Sample 9 is an absorbent article produced by Unicharm Corporation under the tradename MOONY MAN Pull-on.

Sample 10 is an absorbent article produced by Paragon Corporation under the tradename PRIVATE LABEL Pull-on.

Each sample was positioned within a Brookstone No. 2276.00 flexible curve 100 to hold the waist opening of the absorbent article in an open position. Some tension of the waist elastic was required to support the flexible curve. For example, Sample 6 as shown in FIG. 8, having a lateral spacing distance between the two prefastened fasteners along the attachment panel of about 5.0 inches, was positioned within the Brookstone No. 2276.00 flexible curve 100. As shown by the top plan view of FIG. 8, unlike the conventional absorbent articles, the absorbent articles of the present invention have leg openings which are directly below and visible through the waist opening.

The following measurements were taken for each Sample 1 through 10, as shown in Table 3 below. The "Crotch Elastic Spacing" is a measurement of the lateral distance between the outside edge of the elastic members in the crotch region of the chassis. The measurement is taken by opening the waist opening to form a general circle and sliding a ruler through the leg openings to measure the narrowest spacing of the elastic members in the crotch region of the chassis.

The "Relaxed Linear Waist Opening Measurement" is a measurement of the linear inside distance between laterally opposing side edges of the waist opening when the back waist region is directly contacting the front waist region, without stretching the waist opening. In order to eliminate bunching of the front waist region and/or the back waist region, the waist regions were stretched fully three times before taking the measurement. The relaxed waist opening measurement is equal to 2×the relaxed linear waist opening measurement.

The "Relaxed Waist Opening Diameter" is calculated by multiplying the Relaxed Linear Waist Opening Measurement by 2 (which is equal to the relaxed waist opening measurement) and dividing the product by 3.14.

The "Spacing to Waist Diameter Ratio" is the ratio of the Crotch Elastic Spacing to the Relaxed Waist Opening Diameter.

TABLE 3

Comparison of Leg Openings

| Sample # | Crotch Elastic Spacing (cm) | Relaxed Linear Waist Opening Measurement (cm) | Relaxed Waist Opening Diameter (cm) | Spacing to Waist Diameter Ratio |
|---|---|---|---|---|
| 1 | 8.5 | 16.5 | 10.504 | 0.809 |
| 2 | 8.5 | 18.0 | 11.459 | 0.742 |
| 3 | 8.5 | 19.0 | 12.096 | 0.703 |
| 4 | 8.5 | 20.0 | 12.732 | 0.668 |
| 5 | 8.5 | 20.0 | 12.732 | 0.668 |
| 6 | 8.5 | 23.0 | 14.642 | 0.581 |
| 7 | 11.0 | 17.0 | 10.823 | 1.016 |
| 8 | 11.5 | 16.5 | 10.504 | 1.095 |
| 9 | 10.0 | 15.0 | 9.550 | 1.047 |
| 10 | 11.0 | 13.0 | 8.276 | 1.329 |

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. A prefastened, refastenable absorbent article, comprising:
   a chassis having a front waist region, a back waist region and a crotch region intermediate the front waist region and the back waist region, and defining an elasticized waist opening having a relaxed waist opening diameter;
   a first side seam including passive bonds connecting a first edge portion of the front waist region to a first edge portion of the back waist region;
   a second side seam including passive bonds connecting a second edge portion of the front waist region to a second edge portion of the back waist region;
   a first leg elastic member positioned along a first side edge of the chassis at the crotch region; and
   a second leg elastic member positioned along a second side edge of the chassis at the crotch region, the first leg elastic member and the second leg elastic member defining a crotch elastic spacing between an outside edge of the first leg elastic member and an outside edge of the second leg elastic member at a narrowest spacing of the leg elastic members in the crotch region,
   wherein the crotch elastic spacing is less than the relaxed waist opening diameter.

2. The prefastened, refastenable absorbent article of claim 1 wherein the relaxed waist opening diameter is at least about 12.7 mm greater than the crotch elastic spacing.

3. The prefastened, refastenable absorbent article of claim 1 wherein the relaxed waist opening diameter is at least about 20 mm greater than the crotch elastic spacing.

4. The prefastened, refastenable absorbent article of claim 1 wherein a portion of the chassis positioned about a periphery of the elasticized waist opening has an elastic tension not greater than 1400 grams.

5. The prefastened, refastenable absorbent article of claim 1 wherein a first side panel extends in a lateral direction from a vertical axis of the prefastened, refastenable absorbent article at least about 0.635 cm beyond the first leg elastic member in the crotch region.

6. The prefastened, refastenable absorbent article of claim 5 wherein a second side panel extends in a lateral direction from the vertical axis of the prefastened, refastenable absorbent article at least about 0.635 cm beyond the second leg elastic member in the crotch region.

7. The prefastened, refastenable absorbent article of claim 1 wherein a ratio of the crotch elastic spacing to the relaxed waist opening diameter is less than about 1.0.

8. The prefastened, refastenable absorbent article of claim 1 wherein a ratio of the crotch elastic spacing to the relaxed waist opening diameter is less than about 0.85.

9. The prefastened, refastenable absorbent article of claim 1 wherein a ratio of the crotch elastic spacing to the relaxed waist opening diameter is less than about 0.7.

10. The prefastened, refastenable absorbent article of claim 1 further comprising:
    a first fastener and a second fastener, each fastener connected to the front waist region, wherein a lateral spacing between the first fastener and the second fastener is greater than about 25 mm.

11. The prefastened, refastenable absorbent article of claim 10 wherein the lateral spacing is greater than about 50 mm.

12. The prefastened, refastenable absorbent article of claim 10 wherein the lateral spacing is greater than about 100 mm.

13. The prefastened, refastenable absorbent article of claim 1, wherein the chassis further comprises:
    an elastic outer cover;
    an elastic bodyside liner at least partially bonded to the outer cover; and
    an absorbent core positioned between the outer cover and the bodyside liner, the absorbent core having a width in the crotch region of about 2.5 cm to about 12.7 cm.

14. The prefastened, refastenable absorbent article of claim 13 wherein the absorbent core has a width in the crotch region not greater than about 7.6 cm.

15. The prefastened, refastenable absorbent article of claim 13 wherein the absorbent core has a width in the crotch region not greater than about 5.1 cm.

16. The prefastened, refastenable absorbent article of claim 1 comprising a diaper.

17. The prefastened, refastenable absorbent article of claim 1 comprising training pants.

18. The prefastened, refastenable absorbent article of claim 1 comprising absorbent underpants.

19. The prefastened, refastenable absorbent article of claim 1 comprising an adult incontinence product.

20. The prefastened, refastenable absorbent article of claim 1 comprising a feminine hygiene product.

21. The prefastened, refastenable absorbent article of claim 1 comprising a health care garment.

22. The prefastened, refastenable absorbent article of claim 1 comprising swimwear.

23. The prefastened, refastenable absorbent article of claim 1 wherein a relaxed waist opening measurement is about 350 mm to about 400 mm.

24. The prefastened, refastenable absorbent article of claim 1 wherein a ratio of the crotch elastic spacing to the relaxed waist opening diameter is less than about 0.9.

25. A pants shaped prefastened, refastenable disposable absorbent article having a vertical axis, comprising:
    an outer cover;
    a bodyside liner,
    an absorbent core positioned between the outer cover and the bodyside liner;
    a chassis defined by the outer cover, the absorbent core and the bodyside liner, the chassis having a front waist region, a back waist region and a crotch region intermediate the front waist region and the back waist region;
    a first side seam including passive bonds connecting a first edge portion of the front waist region to a first edge portion of the back waist region;
    a second side seam including passive bonds connecting a second edge portion of the front waist region to a second edge portion of the back waist region;
    a first leg elastic member positioned along a first side edge of the chassis at the crotch region;
    a second leg elastic member positioned along a second side edge of the chassis at the crotch region;
    a crotch elastic spacing defined by a lateral distance between an outside edge of the first leg elastic member and an outside edge of the second leg elastic member at a narrowest spacing of the leg elastic members in the crotch region; and
    an elasticized waist opening formed by the chassis having a relaxed waist opening diameter greater than the crotch elastic spacing.

26. The pants shaped prefastened, refastenable disposable absorbent article of claim 25 further comprising at least one fastener prefastened to the front waist region of the chassis.

27. The pants shaped prefastened, refastenable disposable absorbent article of claim 25 wherein an elastic first side panel is laterally positioned with respect to the vertical axis at least about 0.635 cm beyond the first leg elastic member in the crotch region and an elastic second side panel is laterally positioned with respect to the vertical axis at least about 0.635 cm beyond the second leg elastic member in the crotch region.

* * * * *